US00PP35575P2

(12) United States Plant Patent
Conev et al.

(10) Patent No.: US PP35,575 P2
(45) Date of Patent: Jan. 16, 2024

(54) ***ROSA* PLANT NAMED 'VLR13003'**

(50) Latin Name: *Rosa hybrida*
Varietal Denomination: VLR13003

(71) Applicants: Vineland Research and Innovation Centre, Vineland Station (CA); Canadian Nursery Landscape Association, Milton (CA)

(72) Inventors: Rumen Conev, Vineland Station (CA); Parminderjit Sandhu, Vineland Station (CA)

(73) Assignees: VINELAND RESEARCH AND INNOVATION CENTRE, Vineland Station (CA), PART INTEREST; CANADIAN NURSERY LANDSCAPE ASSOCIATION, Milton (CA), PART INTEREST ( * ) Notice: Subject to any disclaimer, the term of this patent is extended or adjusted under 35 U.S.C. 154(b) by 0 days.

(21) Appl. No.: 18/143,962

(22) Filed: May 5, 2023

(30) Foreign Application Priority Data

Dec. 6, 2022 (CA) ..... CA 22-11140

(51) Int. Cl.
*A01H 5/02* (2018.01)
*A01H 6/74* (2018.01)

(52) U.S. Cl.
USPC ..... Plt./108
CPC ..... *A01H 6/749* (2018.05)

(58) Field of Classification Search
USPC ..... Plt./108
CPC ..... A01H 5/022
See application file for complete search history.

*Primary Examiner* — Kent L Bell
(74) *Attorney, Agent, or Firm* — Penny J. Aguirre

(57) ABSTRACT

A new cultivar of *Rosa* plant named 'VLR13003' that is characterized by its flowers that are red in color, its flowers that are medium to large in size, its semi-double to double flowers, its flowers with a subtle fragrance, its upright, bushy plant habit, its foliage that is semi glossy and dark green in color, its good resistance to black spot disease, and its cold hardiness at least to U.S.D.A. Zone 4.

3 Drawing Sheets

Botanical classification: *Rosa hybrida.*
Variety denomination: 'VLR13003'.

CROSS REFERENCE TO A RELATED APPLICATION

This application claims priority to a Canadian Plant Breeder's Rights Application No. 22-11140 filed on Dec. 06, 2022, under 35 U.S.C. 119(f), the entire contents of which is incorporated by reference herein. The Applicant received the information for the Plant breeders' rights application indirectly from the Inventors.

BACKGROUND OF THE INVENTION

The present invention relates to a new and distinct cultivar of *Rosa* of hybrid origin. The new cultivar will be referred to hereafter by its cultivar name, 'VLR13003'. 'VLR13003' is a new cultivar of hybrid rose grown for use as a container and landscape plant.

The new cultivar was derived from a breeding program by the Inventors in Vineland Station, Ontario, Canada. The goal of the breeding was to produce a new cultivar of rose with a cold hardiness to U.S.D.A. Zone 4 and resistance to black spot disease. The Inventor made a cross in 2013 between 'Candelabra' (not patented) as the female and a non-patented plant from the Inventor's breeding program designated as No. 333 as the male parent. 'VLR13003' was selected in 2015 as a single unique plant amongst the resulting seedlings that resulted from the above crosses.

Asexual propagation of the new cultivar was first accomplished by stem cuttings by the Inventors in September of 2015 in Vineland Station, Ontario, Canada. Asexual propagation by stem cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'VLR13003' as a unique cultivar of *Rosa.*

1. 'VLR13003' exhibits flowers that are red in color.
2. 'VLR13003' exhibits flowers that are medium to large in size.
3. 'VLR13003' exhibits semi-double to double flowers.
4. 'VLR13003' exhibits flowers with a subtle fragrance.
5. 'VLR13003' exhibits an upright, bushy plant habit.
6. 'VLR13003' exhibits foliage that is semi glossy and dark green in color.
7. 'VLR13003' exhibits good resistance to black spot disease.
8. 'VLR13003' exhibits cold hardiness at least to U.S.D.A. Zone 4.

The female parent of 'VLR13003' differs from 'VLR13003' in having flowers that are smaller in size and lack fragrance and leaves that are glossy and small in size. The male parent of 'VLR13003' differs from 'VLR13003' in having flowers that are double, medium in size, and light yellow in color and leaves that are glossy. 'VLR13003' can be compared to the *Rosa* cultivar 'Nicolas' (not patented). 'Nicolas' differs from 'VLR13003' in having leaves that are dull and medium green in color, flowers that are slightly smaller and less fragrant, a shorter plant height, and less resistance to black spot disease.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period prior to the filing date. Disclosures include website listings by NVK Nurseries, Bloomin' Easy Plants, Plants Central, Canning Perennials, and Arbor Day.

BRIEF DESCRIPTION OF THE DRAWINGS

The accompanying color photographs illustrate the overall appearance and distinct characteristics of the new *Rosa*. The photographs were taken of a 16-month-old plant of 'VLR13003' as grown outdoors in a 2-gallon container in Park Hill, OK.

The photograph in FIG. 1 provides a close view of an opening flower of 'VLR13003' in bloom.

Figure 1:
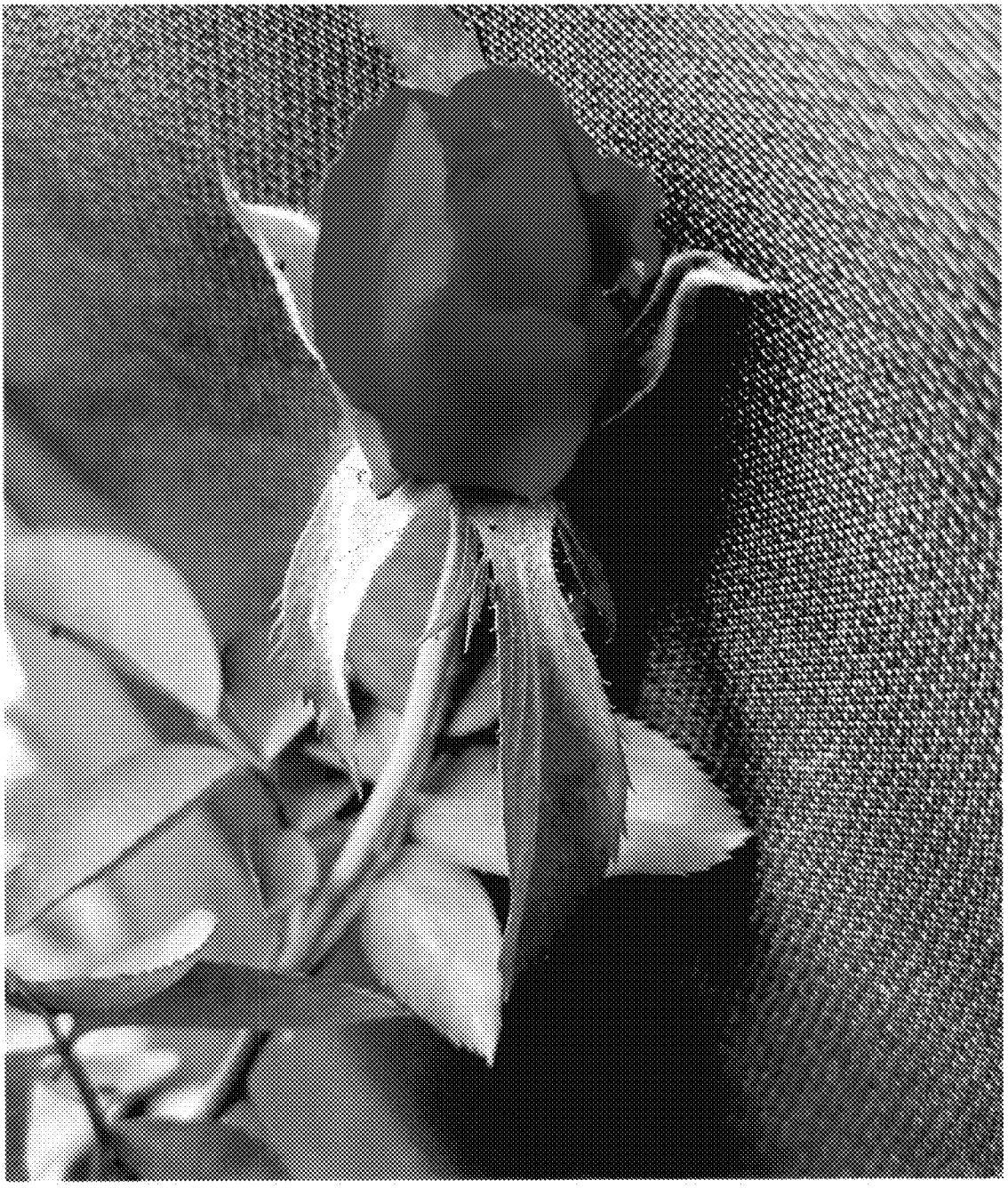
Figure 2:
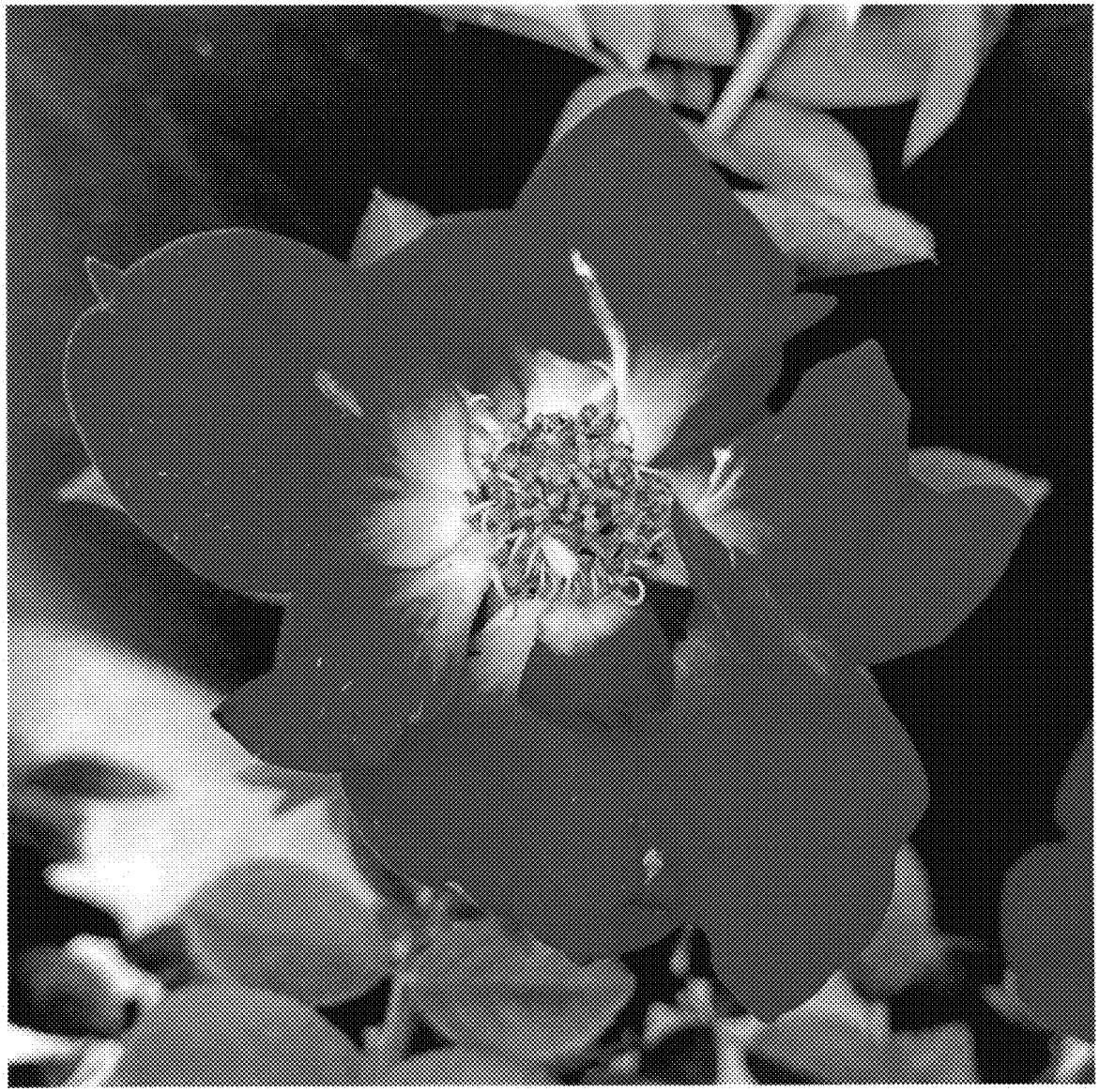

The photograph in FIG. 2 provides a close-up view of a fully open flower of 'VLR13003'.

Figure 3:
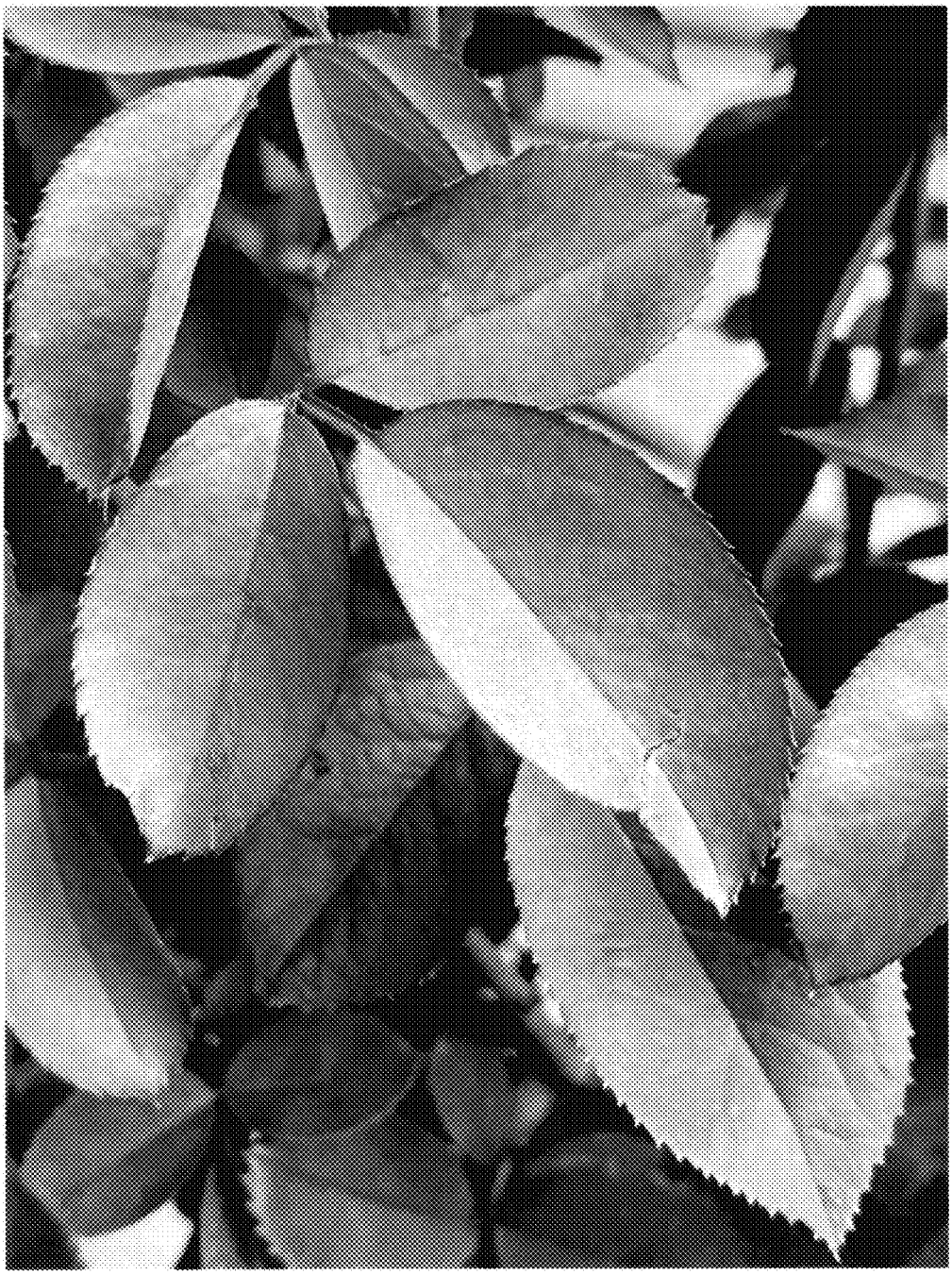

The photograph in FIG. 3 provides a view of the young foliage of 'VLR13003'.

The colors in the photographs are as close as possible with the photographic and printing technology utilized and the color values cited in the Detailed Botanical Description accurately describe the colors of the new *Rosa*.

DETAILED BOTANICAL DESCRIPTION

The following is a detailed description of a 16-month-old plant of 'VLR13003' as grown outdoors in 2-gallon containers in Park Hill, OK. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Continuous bloom from May to September in Ontario, Canada.

*Plant type.*—Herbaceous perennial.

*Plant habit.*—Upright, bushy.

*Height and spread.*—An average of 49 cm in height and 50 cm in spread as a 16-month-old plant and 1 m in height and spread in the landscape.

*Cold hardiness.*—At least to U.S.D.A. Zone 4 (canes will die back at −35° C., but will re-grow in spring).

*Diseases and pests.*—Good resistant to black spot disease (caused by *Diplocarpon rosae*), no resistance or susceptibility to pests has been observed.

*Root description.*—Fibrous, 165B in color.

*Root development.*—An average of 2 to 3 weeks for root initiation with a young rooted plant produced in 8 weeks from a rooted cutting.

*Propagation—Stem cuttings.*

*Growth rate.*—Moderate.

Stem description:

*Stem shape.*—Rounded.

*Stem color.*—Young; 144A, mature; NN137A, old wood and bark; N200A and N200B.

*Stem surface.*—Young and mature; smooth, matte, covered with thorns, old wood and bark; rugose, matte.

*Thorns.*—Sparsely covered with thorns mainly at internodes, sharp pointed, very strong, whorled, an average of 5 per 1 cm, 145C, flushed with 182A, 5 mm in length, at widest point at the base 1 mm in diameter, surface is dull and glabrous.

*Stem strength.*—Strong.

*Stem size.*—Main stems; 23 cm in length, 1 cm in diameter, lateral stems 31 cm in length, 3 mm in diameter.

*Branching.*—Freely branching, held in a moderately upright to slightly outward angles, 13 main stems, 6 lateral stems per main stem.

*Internode length.*—Up to 5 cm.

Foliage description:

*Leaves.*—Pinnate division, alternate arrangement, held in a bowed and outward and downward angle, overall whole leaf shape; ovate, an average of 7.5 cm in length and 6.5 cm in width.

*Leaflets.*—5 per leaf, terminal leaflet; 4 cm in length, 2.5 cm in width, lateral leaflets; average of 2.5 cm in length and 1.5 cm in width, all leaflets; ovate in shape, cuneate base, acute apex, serrate margins, upper surface is smooth, velvety, semi glossy and glabrous, lower surface is rugose and matte, pinnate venation pattern, color: young upper surface; 146A, flushed with 183A, heavily flushed with 183A at the margins, veins are inconspicuous and match surface color, young lower surface; 182A to 182B, veins match surface color, main vein center to base 144B, mature upper surface; NN137A, veins are inconspicuous and match surface color, mature lower surface; 194A, veins are inconspicuous and match surface color.

*Rachis.*—Both surfaces; flattened in shape, concave towards the center to base, up to 1 cm in length, 1 mm in diameter, color; 144B and 145A, young flushed with 183A, surface is glabrous and slightly glossy.

*Stipules.*—Adnate on either side of the petiole, linear in shape, apex is linear and curvy, 1.3 cm in length, 2 mm in width, both surfaces are slightly glossy, glabrous, margins are serrate and densely covered with minute pubescent hairs, 0.2 mm in length, matching surface colors, color; both surfaces 144B, flushed with 180A, especially margins.

*Petioles.*—(Terminal and lateral) both surfaces; flattened in shape, concave towards the center to base, up to 1 cm in length, 1 mm in diameter, color; 144B and 145A, young flushed with 183A, surface is glabrous and slightly glossy.

*Petiolule.*—Both surfaces; Flattened in shape, up to 1.5 mm in length, 0.5 mm in diameter, color; 144B and 145A, young flushed with 183A, surface is glabrous and slightly glossy.

Inflorescence description:

*Inflorescence type.*—Raceme of single flowers on stem terminus.

*Inflorescence shape.*—Ovate.

*Inflorescence size.*—Average of 15 cm in height and diameter.

*Flower number.*—An average of 5 open flowers per receme, average of 32 buds and flowers per plant.

*Flower fragrance.*—Moderate, very pleasant.

*Flower longevity.*—Raceme lasts about 20 days, individual flowers 4 to 5 days.

*Flower type.*—Semi-double to double, rotate.

*Flower size.*—Up to 9 cm in diameter and 4 mm in depth.

*Flower aspect.*—Upright.

*Peduncles.*—Round in shape, strong, up to 5 cm in length, 2 mm in diameter, color; 143B, surface is glabrous, smooth and slightly glossy.

*Flower buds.*—Ovate in shape, up to 3 cm in length, 1 cm in diameter, glabrous surface, color; before burst 144A, flushed with 184A at the top, after burst 144A, flushed with 184A on the sepals, petal portion visible 46A.

*Sepals.*—5, rotate in arrangement, lanceolate in shape, acuminate to acute apex, truncate base, serrate margins, two of the sepals are longer; 4 cm in length and 1 cm in width, three of the sepals are smaller 2.2 cm in length, 5 mm in width, upper surface; two larger sepals; N148A, flushed with 184A, glabrous, matte, three smaller sepals; 143A in color, sheen and densely covered with matted, woolly hairs, NN155D in color, lower surface; two larger sepals; 144A, flushed with 184A, glabrous, matte, three smaller sepals; 144A in color, matte, densely covered with soft, fuzzy, hairs on the margins, slightly translucent and sheen, 0.4 mm in length, NN155D in color.

*Petals.*—10 to 20, persistent, rotate in arrangement, broadly ovate in shape, up to 3 cm in length, 2.7 cm in width, obtuse to rounded apex, entire to slightly undulate margins, cuneate to cordate base, both surfaces are velvety, glabrous and matte, color: upper and lower surface when opening; N45A, upper surface when fully open; 45A, flushed in the center with N57A, base NN155D and 5A, fading to 45B, top N45A, base 9A, lower surface when fully open; 58A to 58B, spot at very base occasionally 9A, fading to 45B, top N45A, base 9A.

*Bracts.*—Simple, attached to base of the long sepals, linear in shape, up to 1 cm in length, 2 mm in width, acute apex, serrate margins, base is cuneate, both surfaces matte, glabrous, color; upper and lower surface 138A, margins flushed with 178A, veins match surface color.

*Receptacle.*—Round, 7 mm in length and diameter, glossy surface, color; 147A.

Reproductive organs:

*Gynoecium.*—Pistil; 1, syncarpous, average of 30 styles with stigmas, stigma is club-shaped, 0.5 mm in diameter, 162C in color, style; up to 5 mm in length, color; top to lower section 44C, base 160C, glabrous and slightly translucent, ovary; oval, 2 mm in length, 1 mm in width, 155B in color, sheen, very densely covered with long thin woolly hairs, up to 1.5 mm in length, 155A in color.

*Androecium.*—An average of 80 stamens, filaments; up to 9 mm in length, 7A in color, anthers; kidney shaped, curved, basifixed, an average of 1 mm in length and 0.6 mm in width, 175A in color, pollen; moderate in quantity and 17A in color.

*Fruit and seed.*—None observed to date.

It is claimed:

1. A new and distinct cultivar of *Rosa* plant named 'VLR13003' as herein illustrated and described.

* * * * *